United States Patent [19]
Bunger et al.

[11] Patent Number: 5,997,833
[45] Date of Patent: Dec. 7, 1999

[54] APPARATUS AND PROCESS FOR PURIFYING HIGHLY IMPURE CALCIUM HYDROXIDE AND FOR PRODUCING HIGH-VALUE PRECIPITATED CALCIUM CARBONATE AND OTHER CALCIUM PRODUCTS

[75] Inventors: James W. Bunger; Don Cogswell, both of Salt Lake City; Jerald W. Wiser, Kaysville, all of Utah

[73] Assignee: James W. Bunger and Associates, Inc., Salt Lake City, Utah

[21] Appl. No.: 09/206,066

[22] Filed: Dec. 4, 1998

Related U.S. Application Data

[62] Division of application No. 08/541,824, Oct. 10, 1995, Pat. No. 5,846,500.

[51] Int. Cl.[6] .............................. C01F 11/00; C01F 11/18; C01B 25/32; C07C 55/06

[52] U.S. Cl. ........................ 423/309; 423/432; 423/490; 423/658.5; 562/597

[58] Field of Search .................................. 423/155, 309, 423/432, 490, 636, 658.5; 562/597

[56] References Cited

U.S. PATENT DOCUMENTS

| | | | |
|---|---|---|---|
| 4,888,160 | 12/1989 | Kosin et al. | 423/432 |
| 5,792,440 | 8/1998 | Huege | 423/432 |

*Primary Examiner*—Wayne Langel
*Attorney, Agent, or Firm*—James L. Sonntag

[57] ABSTRACT

A solution process for the purification of calcium hydroxide, particularly from hydrated carbide lime, which is subsequently used as a feed stock for a high-value calcium product, preferably calcium carbonate. Precipitated calcium carbonate is formed by reaction of the purified calcium hydroxide solution with carbon dioxide in a plug-flow reaction system.

32 Claims, 5 Drawing Sheets

5,997,833

APPARATUS AND PROCESS FOR PURIFYING HIGHLY IMPURE CALCIUM HYDROXIDE AND FOR PRODUCING HIGH-VALUE PRECIPITATED CALCIUM CARBONATE AND OTHER CALCIUM PRODUCTS

RELATED APPLICATIONS

The application is a division of U.S. patent application Ser. No. 08/541,824, filed Oct. 10, 1995 U.S. Pat. No. 5,846,500.

FIELD OF THE INVENTION

This invention relates to an apparatus and process for the production of calcium carbonate from hydrated carbide lime.

BACKGROUND OF THE INVENTION

In the currently practiced processes for making acetylene, calcium carbide is charged to a tank containing water. The carbide is dropped onto the surface of the water where it is allowed to react spontaneously. Acetylene gas is withdrawn from the top of the tank while calcium hydroxide and other impurities settle to the bottom of the tank.

The calcium hydroxide product, along with impurities, is discharged, stockpiled and disposed of as a secondary, low-value by-product $Ca(OH)_2$, also known as hydrated carbide lime. In the current acetylene processes, disposal of the hydrated carbide lime by product, which actually weighs more than the calcium carbide imported into the plant, is becoming increasingly difficult to dispose of because of environmental regulations. The most common usage of hydrated carbide lime is to neutralize industrial acid streams for pH control. Hydrated carbide lime is also used for pH control in sewage treatment facilities. Such applications are of low value and transportation over very large distances becomes prohibitively expensive.

According to the Compressed Gas Association, Inc. (publication #CGA-1.5-1991) other applications of hydrated carbide lime are dehalogenation, metallurgical extractions, gas scrubbing, desulphurization, gas manufacture, masonry additives and as a reagent for manufacture of calcium hypochlorite (a bleach) and calcium magnesium acetate (a deicing agent). Except for these latter two commodities which gain much of their value from the importation of reagents ($Cl_2$ and $Mg^{+2}$/acetic acid, respectively), all of these uses are low value, probably less than about $50/ton in 1995 dollars.

There are many calcium products currently being marketed, most of which are the inorganic or organic salt of a corresponding acid. Calcium salts currently being marketed derive their calcium from some source other than hydrated carbide lime. This is due in large part to the impurities in the hydrated carbide lime, such as metals, slag, minerals and carbon which come from the coal, coke and limestone used in the calcium carbide manufacturing process. These impurities have heretofore rendered hydrated carbide lime unsuitable as a feed stock for the manufacture of many purified calcium products.

One finished calcium product of particular interest is purified precipitated calcium carbonate (PCC), which is salable in a growing market at high value. A process for manufacture of PCC from hydrated carbide lime would enjoy market, environmental and economic advantages over currently practiced technology.

OBJECTS OF THE INVENTION

It is, therefore, an object of the invention is to maximize the value of hydrated carbide lime and to provide a process for the production of purified calcium carbonate from hydrated carbide lime.

It is further an object of the invention to provide a method for producing a clean lime solution from a hydrated carbide lime feed stock.

It is further an object of the invention to produce precipitated calcium carbonate from clean lime solution derived from hydrated carbide lime.

It is further an object of the invention to provide a method for the control of the crystal size and morphology of precipitated calcium carbonate produced from lime solutions.

It is further an object of the invention to provide a method for making a variety of higher-value products from hydrated carbide lime.

It is further an object of the invention to provide a method for producing a clear purified lime solution.

SUMMARY OF THE INVENTION

The invention involves the purification of impure hydrated carbide lime to produce purified calcium hydroxide and the production of high-value calcium materials therefrom. While the invention is directly applicable to the purification of very impure hydrated carbide limes, purification of other impure calcium hydroxide materials is also contemplated.

An embodiment of the invention is a method for purifying hydrated carbide lime which is the reaction product of calcium carbide and water, the method comprising;

(a) diluting the hydrated carbide lime with water to dissolve solid calcium hydroxide to form a solution of calcium hydroxide with a concentration at or below the saturation concentration of calcium hydroxide, (b) separating remaining solid materials by gravity separation by introduction of the solution from (a) into a quiescent environment sufficient to allow gravity separation of floatable solids that rise to the top surface of the solution and rapidly settling solids that sink to form a sludge and withdrawal of the floatable solids and the sludge containing the sinking solids, (c) filtering the resultant solution of calcium hydroxide of step (b) to remove solids remaining after the separation in step (b), (d) contacting the filtered solution from step (c) with $CO_2$ gas under plug-flow cocurrent conditions and at a temperature to form calcium carbonate crystals predominantly of the calcite form, i.e., between about 5° C. and 25° C., (e) introducing flocculation aids into the resultant slurry of calcium carbonate crystals of step (d) to promote weak association of the calcium carbonate crystals, (f) dewatering the associated calcium carbonate crystals by gravity separation in which the resultant of step (e) is introduced into a quiescent environment sufficient to allow settling of the associated calcium carbonate crystals to form an essentially clear solution and to form a thickened slurry of the associated calcium carbonate crystals, (g) withdrawing the resultant clear solution from step (f) and recycling the clear solution as a source of water for step (a), (h) filtering or centrifuging the thickened slurry resulting from step (g) to further remove water to form a thickened slurry or an essentially solid filter cake of calcium carbonate crystals, and withdrawing and recycling the filtrate as a source of water for step (a), and (i) optionally drying the resultant of step (h) by evaporating the water from the calcium carbonate crystals in the filter cake under conditions to remove moisture therefrom.

The method of the invention departs from conventional practice of manufacturing calcium salts, particularly precipitated calcium carbonate, in a number of points. In particular, hydrated carbide lime is not currently being used as feed stock for high-value calcium derivatives. This is due to the highly contaminated state of hydrated carbide lime, usually having dry $Ca(OH)_2$ content of about 95 wt. % or less. Since alternate sources that are purer are available, such as high-grade limestone, sources such as hydrated carbide lime that require extensive purification are avoided. However, with the fairly high production of hydrated carbide lime as a by product of acetylene manufacture, the process of the invention provides a viable use for this material that is typically regarded of little value.

Another point of departure is the use of a cocurrent-plug flow reaction system to form the precipitated calcium carbonate. In conventional crystallizers, the reaction system is generally mixed or stirred in a batch-type system. In the present invention, a cocurrent plug flow system is used to exploit the kinetics of calcium carbonate crystal formation growth and to improve the uniformity of the crystal size distribution.

The plug flow reaction system permits a better control over the crystal size distribution in the product. This is possible because the residence time and reactant concentrations can be controlled throughout the crystal growth process. The result is a size distribution where the size of smallest crystals differ from the largest crystals by a factor of only about three. This compares with currently available commercial products wherein the size distribution range is factor of about ten.

The plug flow reaction system also allows the crystal to be grown in different predetermined reaction systems during its growth. This can be done by providing a reaction in two or more plug-flow reaction stages. Each stage may have a different amount of $CO_2$ and/or a different system of additives to control crystal growth and morphology. Greater control over the system may also be provided by having a plurality of carbon dioxide injection sites along the length of the plug flow reactor.

Yet another point of departure is the use of solution processing in the present invention. In conventional practice where partially soluble materials are involved, the amount of water necessary to create a solution is regarded as too large for economic reasons. For example, for calcium hydroxide, a slurry is processed to lower the water needs for the system, so as to minimize the pumping costs, reactor size, and the like. In addition, crystallization of calcium carbonate from dilute solutions requires much longer settling times, and hence larger settler residence times and greater settler volumes. However, the present invention is a successful and economically viable solution system, due principally to means to accelerate settling of the calcium carbonate by careful selection of flocculating agents which allow for rapid association of crystallites and by recycling water from the dewatering and filtration of the calcium carbonate to dissolve the hydrated carbide lime. The rate of settling may be further enhanced by recycling some of the settled particles to increase the solids density in the flocculation steps.

As a solution system, the present invention provides advantages over conventional slurry or solid systems. The material to be purified, the calcium hydroxide, is totally in solution, thus it is simpler to remove impurities that remain as solids. For hydrated carbide lime and indeed for hydrated lime from mined limestone or most industrial streams, this is essentially all of the impurities present, thus a highly pure calcium hydroxide solution can be made, that in turn can be used to form a high-purity, high-value calcium carbonate product.

In the method of the invention the calcium hydroxide solution is highly dilute. (The solubility of $Ca(OH)_2$ is only 0.185 g/100 g water at 0° C.) Therefore, when the solution is reacted to precipitate a less soluble calcium product, such as the reaction with carbon dioxide to produce calcium carbonate, the precipitated product is separated from any impurities that may be dissolved in the calcium hydroxide solution. In the preferred embodiment, precipitated calcium carbonate is fractionally precipitated away from more soluble salts that remain in solution. Thus, by practice of the present invention a very pure product can be produced, even though the hydrated carbide-lime feedstock is very impure. This is achieved in large part by the solubilization to calcium hydroxide to separate insoluble impurities, and a fractional precipitation to separate soluble impurities.

The method of the invention, accordingly, is also useful to purify any calcium hydroxide/oxide that contains solid, insoluble impurities, as is hydrated carbide lime, and such materials are contemplated to be within the scope of the invention. Calcium hydroxide/oxide materials that contain significant impurities that will not form solids when the calcium hydroxide is solubilized, e.g., soluble inorganic impurities, certain organic pollutants, and the like, have varying solubility properties and depending upon these properties and their concentrations may not be suitable for the invention.

In ordinary acetylene processes, the hydrated carbide lime contains impurities such as metals, slag, minerals and carbon which come from the coal, coke and limestone used in the calcium carbide manufacturing process. The present invention addresses the requirement of cleaning the impurities from hydrated carbide lime. The present invention also provides the means for converting hydrated carbide lime to a more valuable calcium-based product.

Another advantage of a solution reaction system and compared to a slurry reaction system, is that the reaction time of $CO_2$ with calcium hydroxide in solution is much faster than with solid calcium hydroxide in a slurry. The reaction times in the present invention are on the order of seconds, compared with tens of minutes up to an hour or more with slurry systems.

Other advantages of solutions systems over slurry systems are the reduction in stirring energy and better control of the reaction and the better control over the reaction system. This is because in the plug-flow system, at any point or coordinate along the system or reaction path from initial introduction of carbon dioxide until the formation of the associated crystals, the progress of the reaction at the reaction coordinate is precisely know. Even if applied to a slurry system, a plug-flow system would not provide as much control as it does in the present invention because in a slurry system there is always a situation where there is a distribution of events along the reaction coordinate. For example, in a slurry system the reaction rate of the calcium hydroxide and the carbon dioxide will depend upon the rate of dissolution of the calcium hydroxide slurry into solution, which cannot be precisely predicted or controlled. In contrast, in the present solution reaction system, the reactants are already in solution and properties of the system, such as the reactions rates, concentrations, etc., are more precisely determinable.

While, the preferred calcium-containing compound produced by the present invention is calcium carbonate, the present process is suitable for the production of certain other calcium compounds that can be produced from $Ca(OH)_2$. Such compounds are those that have a very low solubility in water, specifically those less soluble than $Ca(OH)_2$. Examples of such compounds include, but are not limited to those shown below in Table A. Also shown is a possible reagent for reaction with $Ca(OH)_2$ to produce the compound. The reagents shown are illustrative and may not be the most cost effective reagents to obtain the product.

TABLE A

Examples of Calcium Products from Calcium Hydroxide Produced from a Solution System

| Calcium Product | Reagent |
|---|---|
| Carbonate | $CO_2$ |
| Fluoride | HF |
| Oxalate | Oxalic Acid |
| Diorthophosphate | $H_3PO_4$ |

An economic criterion for production of calcium-based products from hydrated carbide lime is that they have a high market value in relationship to the cost of reactants. The price/cost relationship establishes a measure of the potential value. In the present process, the source of the $Ca(OH)_2$ reactant is generally the low-cost by-product of an acetylene process. Accordingly, the production cost depends mostly on the cost of the other reactants. It has been found that as a general rule that a higher mass contribution from the $Ca(OH)_2$ and a lower mass contribution from other reactants will produce a more commercially viable product. For example, for $CaCO_3$, the first product in Table A, the contribution of $Ca(OH)_2$ to the final product, $CaCO_3$, is 56 wt. %. In contrast, for the other calcium products the contribution is lower. Thus, more of the value for these calcium products that derives from the anionic reactant. The process is commercially viable only if the calcium product has a higher value than the reactant reacted with the calcium hydroxide.

The order of the listing in Table A shows the ranking of higher mass contributions to lower mass contributions. Heading the list is calcium carbonate. Calcium carbonate is afforded this advantage because of the relatively low molar mass of the anion ($CO_3^{-2}$) and the fact that effectively one of the oxygen atoms contained in the $Ca(OH)_2$ is used in the final product. In other words, more calcium-based product is made from a given amount of reactant ($CO_2$) than any other commonly traded product. In addition, the reactant, $CO_2$ is easily and cheaply obtained as a by-product of combustion of fossil fuels that may be used for energy in the drying process.

In current practice $CaCO_3$ is not produced using hydrated carbide lime from an acetylene process. Instead, precipitated $CaCO_3$ is made by reacting $CO_2$ with hydrated lime produced from mined materials that are already free of large amounts of contaminants. (See for example, U.S. Pat. No. 4,367,207) These hydrated lime sources usually have a $Ca(OH)_2$ content exceeding 96 wt. % or more. In summary, the hydrated lime is prepared by a special process to ensure its quality and reactivity by the following reaction sequence:

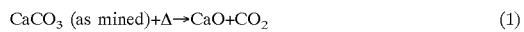

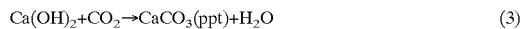

This is a cumbersome process and requires substantial energy to convert the limestone ($CaCO_3$) to lime (CaO) in reaction (1). Additionally, calcium must be transported in several stages beginning at the mine, then to a central process facility and to the place where it is precipitated and finally to the end user.

The $CaCO_3$ of the invention is of high market value and solves an historic problem with disposal of low-value hydrated carbide lime from acetylene processes.

DETAILED DESCRIPTION OF THE INVENTION

The present process is adapted to the purification of hydrated carbide lime, which is the by product of acetylene production processes wherein calcium carbide and water are reacted. As it comes from the acetylene process, it typically contains a multitude of impurities that render it unsatisfactory as a feed stock for a number of processes where purity is an important consideration. These impurities are in large part introduced through the original calcium carbide, and comprise mineral substances, metal, and carbon particles originating from coal, coke, and the like. The process of the invention is suitable for treatment of any hydrated carbide lime by product and other hydrated lime materials not derived from calcium carbide.

Figure 1:
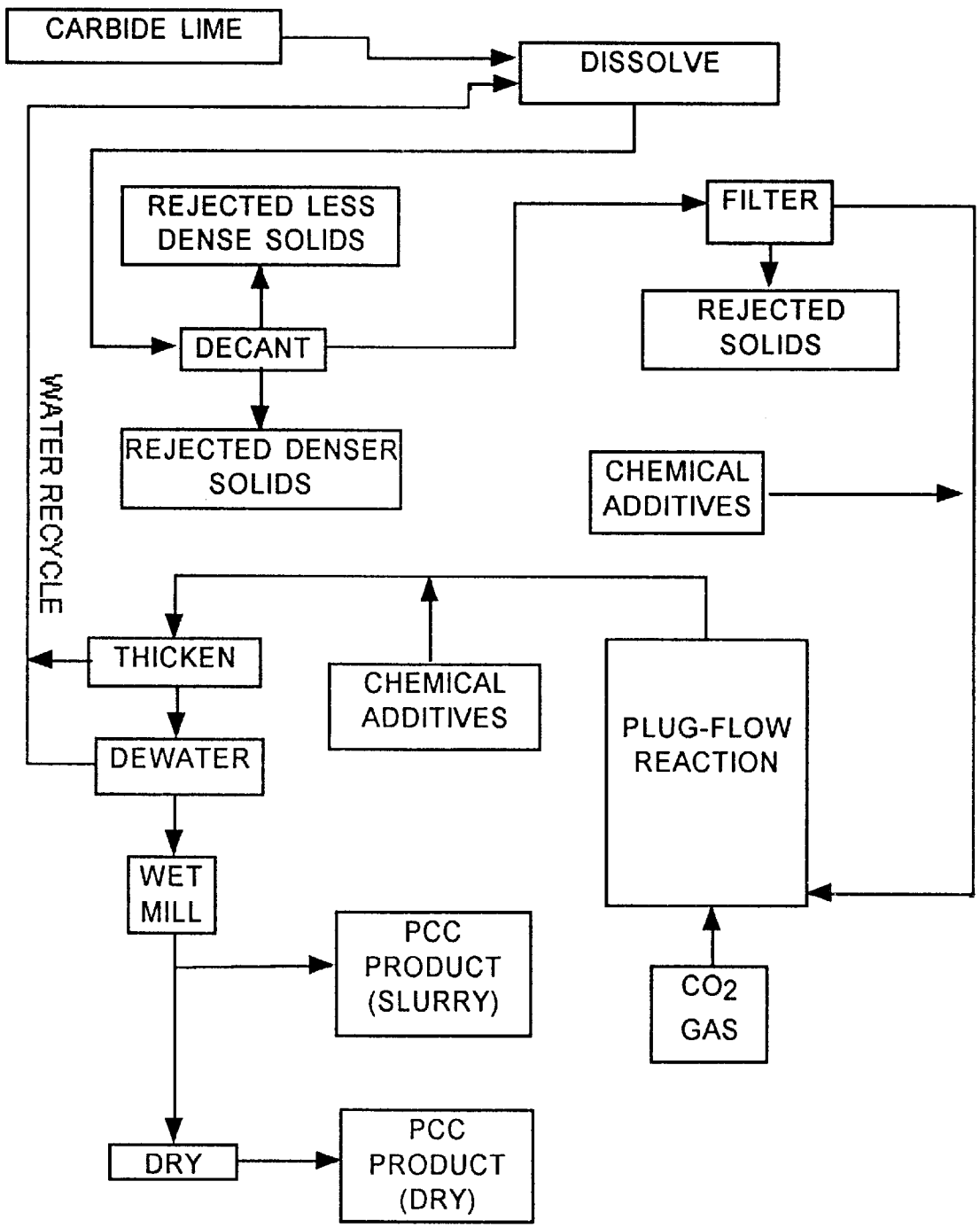
FIG. 1 is a flow-sheet illustrating a calcium carbonate process of the invention.

Referring to FIG. 1, the hydrated carbide lime is first diluted with water to dissolve essentially all of the calcium oxides and hydroxides and form a solution. The calcium hydroxide concentration is at or below the saturation concentration to allow essentially all of the calcium oxide and hydroxide to dissolve. Preferably the concentration is at or near saturation to minimize the solution volume and to provide maximum thermodynamic driving force for subsequent crystal nucleation.

Solid materials are then separated using a gravity settling and clarifying technique. Rapidly settling solids that are more dense than the calcium hydroxide solution and are removed from the bottom. The floatable materials rise to the top. Conventional settling and clarifying equipment can be used, such as continuous clarifier vessels with circular rakes in the bottom for withdrawing the sludge containing the more dense solids from the bottom, and skimmers for withdrawing the less dense solids from the top. Because of the low solids content of the calcium hydroxide solution, it is desirable to incorporate features to accelerate the settling and thereby lower the residence time and total volume of solution in the clarifier. A passive clarifier of the inclined plate settler type or alternatively a DELTASTAK™ clarifier, available commercially, will adequately perform this function. Conventional additives to aid settling and/or floating may also be added to the solution.

The middling stream or clarified solution is then filtered to remove any remaining solids. Preferably the filtration is staged to remove larger particles first with each succeeding stage having a finer filter medium. Preferably the final filtration will be about a $1\mu$ filter or less. The removed deposits may be removed from the filter media by conventional techniques, such as by backwashing with an acid wash, or by mechanical scraping, or both.

The calcium hydroxide in the filtered solution is then reacted with carbon dioxide gas to form calcium carbonate. This is done by contacting the solution with carbon dioxide in a cocurrent plug-flow reaction scheme. Any suitable reactor system is contemplated, e.g., vertical gas reactor, in-line mixers, or the like. The requirement is that the reactants and product have little mixing in the same or the axial direction of the cocurrent flow, with mixing to promote the reaction in the radial direction, the direction perpendicular to the reactant flow. While some mixing in the axial direction is inevitable, the plug-flow reaction system of the invention contemplates the dominant mixing in the radial direction while minimizing mixing in the axial direction.

Figure 2:
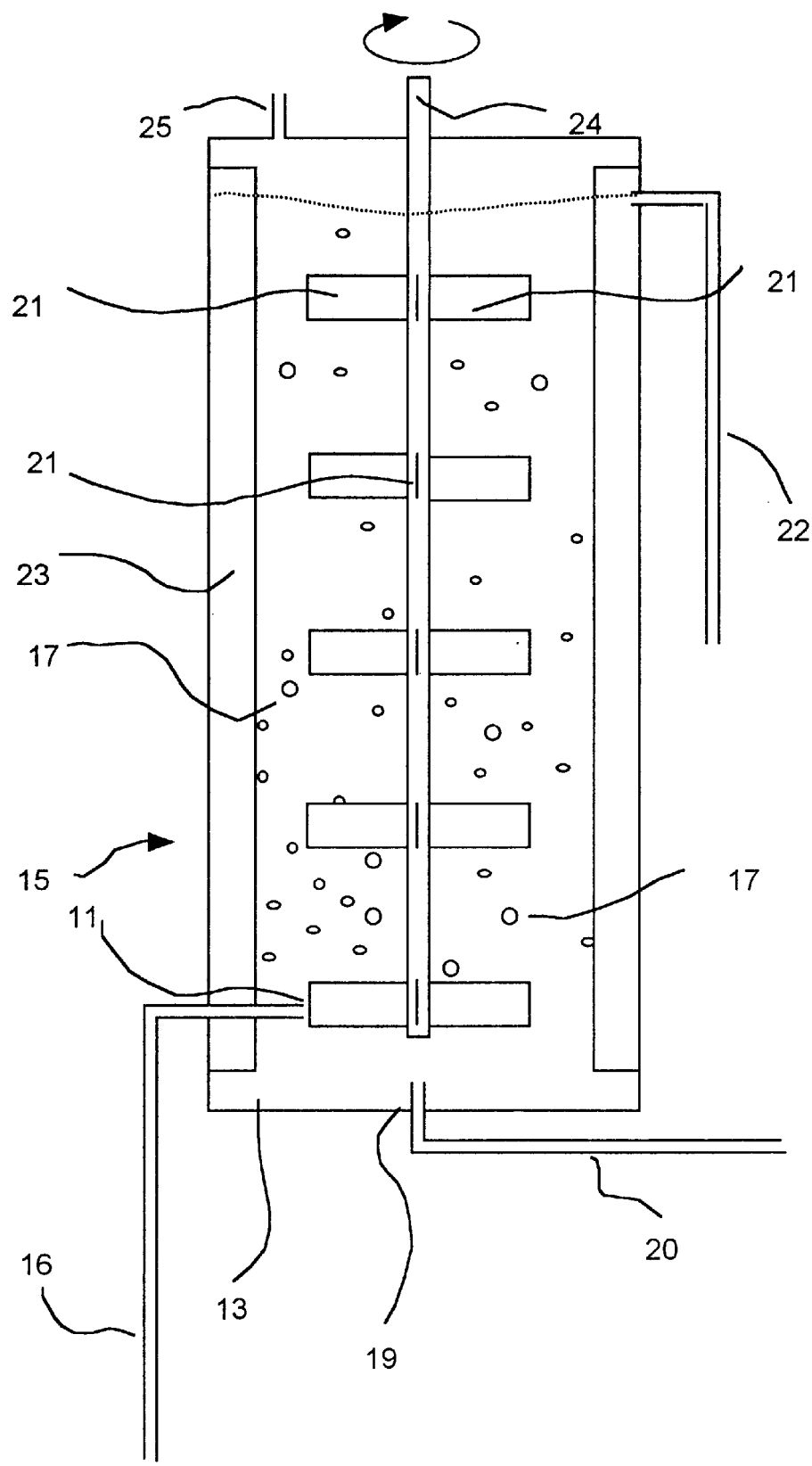
FIG. 2 is a simplified cross-sectional diagram of a cocurrent reactor used in the method of the invention.

The cocurrent reaction system is best accomplished by introducing the solution and dispersing carbon dioxide in the bottom of a vertical reactor as illustrated in FIG. 2. The carbon dioxide is introduced or dispersed at 11 near the bottom 13 of the reactor 15 through line 16. The reactor 15 is generally cylindrical on a vertical axis. The carbon dioxide entry point 11 is preferably near tip of the high sheer zone at the outer edge of the non-pumping agitator 21 to aid in dispersion and to reduce calcium carbonate scaling on the reactor walls. Additional entry points for the carbon dioxide may also be provided, preferably near the tips of agitators further up the reactor. The carbon dioxide is dispersed as small bubbles 17 which is dissolved in the solution. A flow of the calcium hydroxide solution is also introduced near the bottom 13 at 19 through line 20 and directed upwards in the same direction as the rising carbon dioxide gas bubbles. The dispersed carbon dioxide bubbles dissolve in water where the dissolved ions react with dissolved calcium hydroxide to form calcium carbonate. Since the calcium carbonate is less soluble than the calcium hydroxide it forms in the form of a slurry, which is withdrawn at the top through line 22. The reactor is agitated using agitators 21 that mix mainly in the radial or horizontal direction, as opposed to the axial or vertical direction in the direction of flow. The agitators 21 are preferably flat paddles with no pitch turning on vertical shaft 24, to provide as nearly as possible a plug flow of the solution with minimized mixing in the forward and reverse directions. Mixing is also enhanced by providing fixed vertical baffles 23 attached to the inner wall of the reactor 15.

In order to achieve sufficient residence time in the reactor, the reactor may be lengthened, or two or more reactors may be placed in series. In a series scheme, the length to diameter ratio of the reactors may be optimized for operability. Any unreacted carbon dioxide is withdrawn through 25 and recycled.

The reason for the cocurrent plug-flow reaction system is to exploit the reaction kinetics of the system to preferentially produce relatively small, uniformly sized $CaCO_3$ crystals. It has been found that if there is a large driving force toward crystal formation/nucleation, e.g., by a high concentration of both reactants, new crystals are preferentially formed as opposed to a growth of existing crystals. On the other hand, if the driving force is small, e.g., one reactant ($CO_2$) is gradually introduced over the length of the reaction, crystal growth is preferred to nucleation.

Thus, the best reaction for uniform and small crystals is to start with a high driving force for crystal formation, followed by a smaller driving force for crystal growth. This is achieved by a cocurrent reactor where the $CO_2$ and $Ca(OH)_2$ reactants are mixed at a maximum concentration. When first contacted, the reaction is very rapid forming a large number of very small crystals. The stream, now depleted of reactants, favors crystal growth. Growth of the initially formed crystals is favored, rather than new crystal formation. By adding and dispersing $CO_2$ in the proper stoichiometric amount and avoiding back mixing or axial mixing, the crystals are of uniform and small size.

In contrast, in a continuous stirred-tank reactor system., the reactants are continuously backmixed, mixing solution depleted of reactants with new solution entering the system. The driving force for nucleation is only modest, and significant crystal formation and crystal growth occurs throughout the residence time of the reacting solution. Thus, the crystal distribution is wide, ranging from small newly formed crystals to large, older crystals. This leads to wide variations in the progress of reaction and results in crystals of wide size distribution.

The higher valued form of calcium carbonate is calcite, which is preferentially formed at lower temperature, 30° C. or less, preferably between 5° C. and 25° C. The reaction stream may also be treated with known additives to aid desirable crystal formation, association, and/or size distribution. The solubility of calcium carbonate is much lower than that of calcium hydroxide; thus, the calcium carbonate readily precipitates from the solution forming a slurry in the reacted solution.

Immediately after reaction, the calcium carbonate slurry is preferably treated with conventional additives to prevent fusing of the crystals, or disproportionation growth, i.e., the redissolving of small thermodynamically unstable crystals and the reprecipitation of the redissolved $CaCO_3$ on other crystals until they become more thermodynamically stable and to promote association of the crystals. Suitable additives to control the thermodynamic stability are polycarboxylic acids. An example of such a polycarboxylic acid is polypropenoic acid, such as CP-10, available from BASF. Other additives may be used to accomplish the same objective.

It is also contemplated in the invention to used crystal growth modifiers to control the size and morphology of the crystals. These materials are incorporated in the crystal or interfere with the surface so as to interfere with growth kinetics and growth morphology. Preferably, the process is controlled to produce a crystal size range from 0.1 microns to 5 microns, although narrower ranges are possible by practice of the invention, e.g., from 0.1 to 0.3, or 1 to 2 microns. Suitable crystal growth modifiers include various polyphosphonic acids and dibasic calcium phosphate. An example of a polyphosphonic acid is hexamethylenediamine-tetra(methylene-phosphonic acid) (HMDTMP) available under the name Briquest™ from Albright & Wilson. This material inhibits the growth of formed crystals to prefer formation of new crystal nuclei. The result is a generally small crystal size. As another example, addition of dicalcium phosphate discourages formation of spherical crystals with preference toward rhombohedral or scalenohedral (needle-like) crystals, depending upon the concentration of the dicalcium phosphate. Other additives are contemplated that affect crystal size and morphology.

The calcium carbonate slurry is then concentrated by introduction into a settling environment, using conventional settler/clarifier and thickener technology. The rate of settling may be enhanced by use of cationic, anionic or non-ionic flocculating agents. Examples of flocculating chemicals are cationic floc or anionic floc W-37 marketed by Allied Colloids. A clear solution is drawn from the top of the settler and preferably recycled as a water source to dissolve the hydrated carbide lime.

The dewatered or concentrated sludge is then filtered by conventional means to form essentially solid filter cakes, which are purified calcium carbonate. The filtrate is also preferably recycled as a water source for dissolving the hydrated carbide lime. If water soluble impurities are present, these impurities may be removed from the recycle streams using conventional water-treatment technologies.

The dewatered particles in the filter cake are then dried to form an anhydrous product. The drying is by any suitable means, such as a ring dryer, drum dryer or spray dryer. Before drying the dewatered particles may optionally be wet-milled by conventional techniques to disassociate or disperse the particles. In addition, the particles may by coated by known additives before drying, including but not limited to, dispersants such those of the polycarboxylic acid type.

When appropriate and feasible, materials may be stored between process steps to provide a surge capacity. For example, the hydrated carbide lime slurry may be stored before introduction into the dissolver. In addition, the dry calcium carbonate product may be stored before bagging, or shipping operations.

The purity of the calcium carbonate product meets the highest industrial standards, e.g., for use as whiteners in paper making, paints, pigments, plastics, and the like. The calcium carbonate is bagged or shipped by conventional techniques according to industry practice.

Process Control

In general, the value of the $CaCO_3$ product increases as the size of the $CaCO_3$ particles decreases. The value also increases with increasing brightness and with increasing dryness. The calcite form of the $CaCO_3$ crystal is preferred to the aragonite form because of the greater thermal stability and brightness of the calcite form.

An effective process is one which takes these objectives into account and is so configured as to provide the smallest and whitest particle and to dry the product as price/cost benefits allow.

EXAMPLES

Example I

A process of the invention was conducted, essentially as described in the description above. The hydrated carbide lime used was from a wet acetylene process. An anionic high molecular weight flocculent, suitable for pH environments between 8 and 11 (Flocculent W37, available from Allied Colloids) was used in the settler.

The calcium carbonate product was analyzed physically and chemically from a series of runs by conventional techniques. Typical results are summarized in Table B;

TABLE B

| Precipitated Calcium Carbonate | |
|---|---|
| Typical Physical Analysis | |
| Brightness | 95.0% |
| Specific Gravity | 2.55 |
| pH | 9.5 |

TABLE B-continued

| Precipitated Calcium Carbonate | |
|---|---|
| 325 mesh residue | <0.01% |
| Crystal Type | Calcite |
| Particle Size (95%) | <1 μm |
| Typical Chemical Analysis | (weight percent) |
| Calcium Carbonate, $CaCO_3$ | 97.82 |
| Acid Insolubilities | 0.07 |
| Magnesium, Mg | 0.30 |
| Sulfate, $SO_4$ | 0.17 |
| Iron, Fe | <0.01 |
| Silicon Dioxide, $SiO_2$ | 0.92 |
| Aluminum Oxide, $Al_2O_3$ | 0.67 |
| Others | 0.05 |

Example II

A process of the invention was conducted, essentially as described in the description above. Dry carbide lime was added to soft water at a concentration of about 3.3 grams lime per liter water, and stirred. An analysis of the carbide lime is shown below in Table C;

TABLE C

| Analysis of Carbide Lime | |
|---|---|
| | (wt. %) |
| $Ca(OH)_2$ | 80.5 |
| $SiO_2$ | 3.4 |
| $Al_2O_3$ | 1.9 |
| $Fe_2O_3$ | 0.2 |
| $Na_2O$ | 0.7 |
| $P_2O_5$ | 0.7 |
| All Other Minerals | 1.0 |
| Carbon (as coke) | 3.6 |
| Moisture | 8.0 |
| TOTAL | 100.0 |

The resulting solution/slurry was sent to a decanter where insoluble material was allowed to settle or float. A clear stream is then removed from below the surface. The resulting fluid was filtered through a 0.3μ filter. A polyphosphonic acid was introduced to the solution at 0.00029 wt. % of the solution.

The solution was continuously introduced to a plug-flow reaction system and carbon dioxide gas was introduced to the reactor in sufficient quantities so that the pH at the end of the reaction was between 9.5 to 9.7.

After introduction of the carbon dioxide, a polypropenoic acid was added at a rate 0.0310 wt. % of the total solution and allowed to mix in an in-line mixer.

A cationic flocculating agent (#368) was continuous added at a rate 13 ppm to "gather" the crystals where they were allowed to settle in the thickener. Supernatant water was decanted. The thickened PCC could be used as is or sent to a dryer.

The calcium carbonate product was analyzed physically and chemically from a series of runs by conventional techniques. The results of the analy:sis are shown below in Table D.

TABLE D

Analysis of PCC

| Property | Value |
| --- | --- |
| Crystallite Size Range by SEM 10–90% ($\mu$m) | 0.1–0.3 |
| Particle Size Range Electrophoresis ($\mu$m) | 1.0–5.0 |
| Median Particle Size by Electrophoresis ($\mu$m) | 1.6 |
| Brightness | 96.7% |
| $CaCO_3$ (wt. %) | 98.0 |
| $SiO_2$ (wt. %) | 0.7 |
| $Al_2O_3$ (wt. %) | 0.6 |
| MgO (wt. %) | 0.3 |
| $Fe_2O_3$ (wt. %) | <0.01 |
| All Other (wt. %) | 0.4 |

Figure 3A:
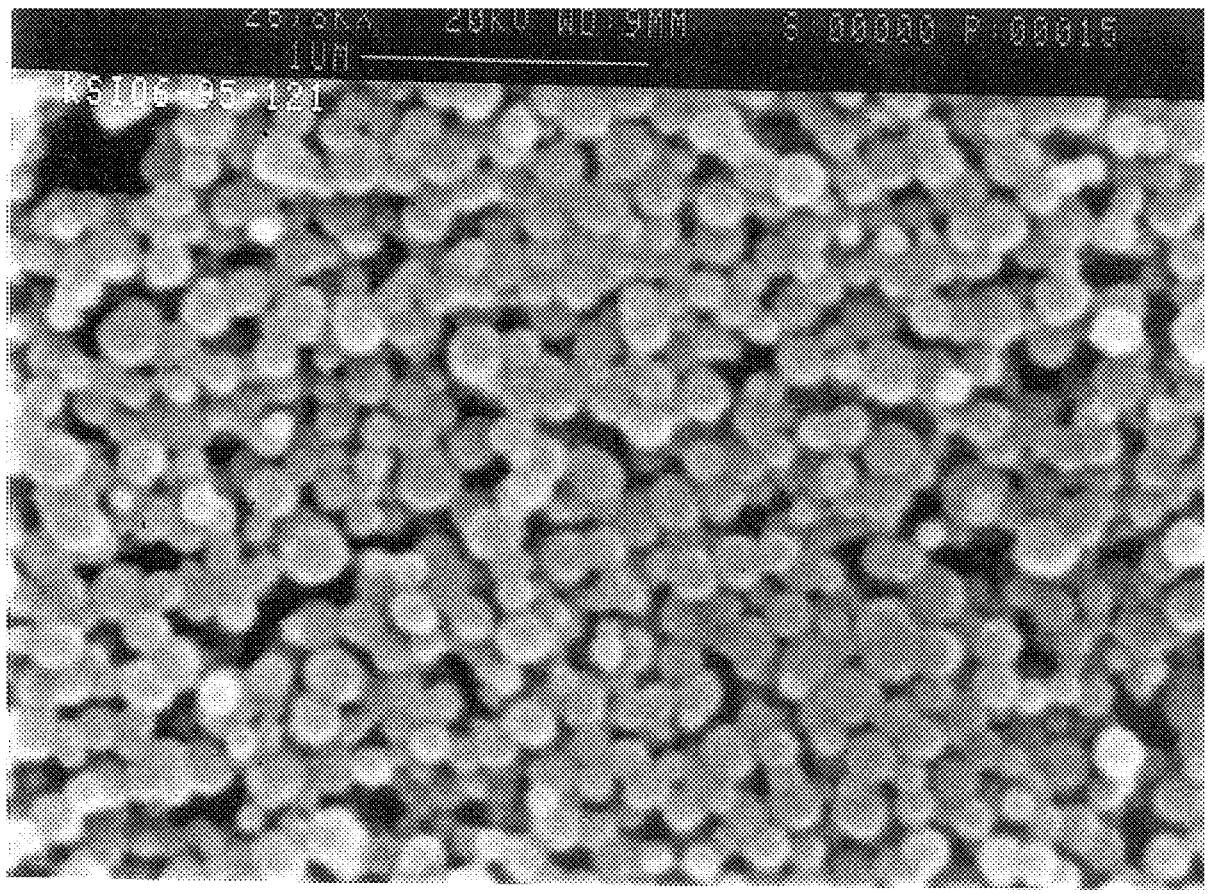
FIGS. 3a to 3c are electron micrographs showing precipitated calcium carbonate produced by the invention.
Figure 3B:
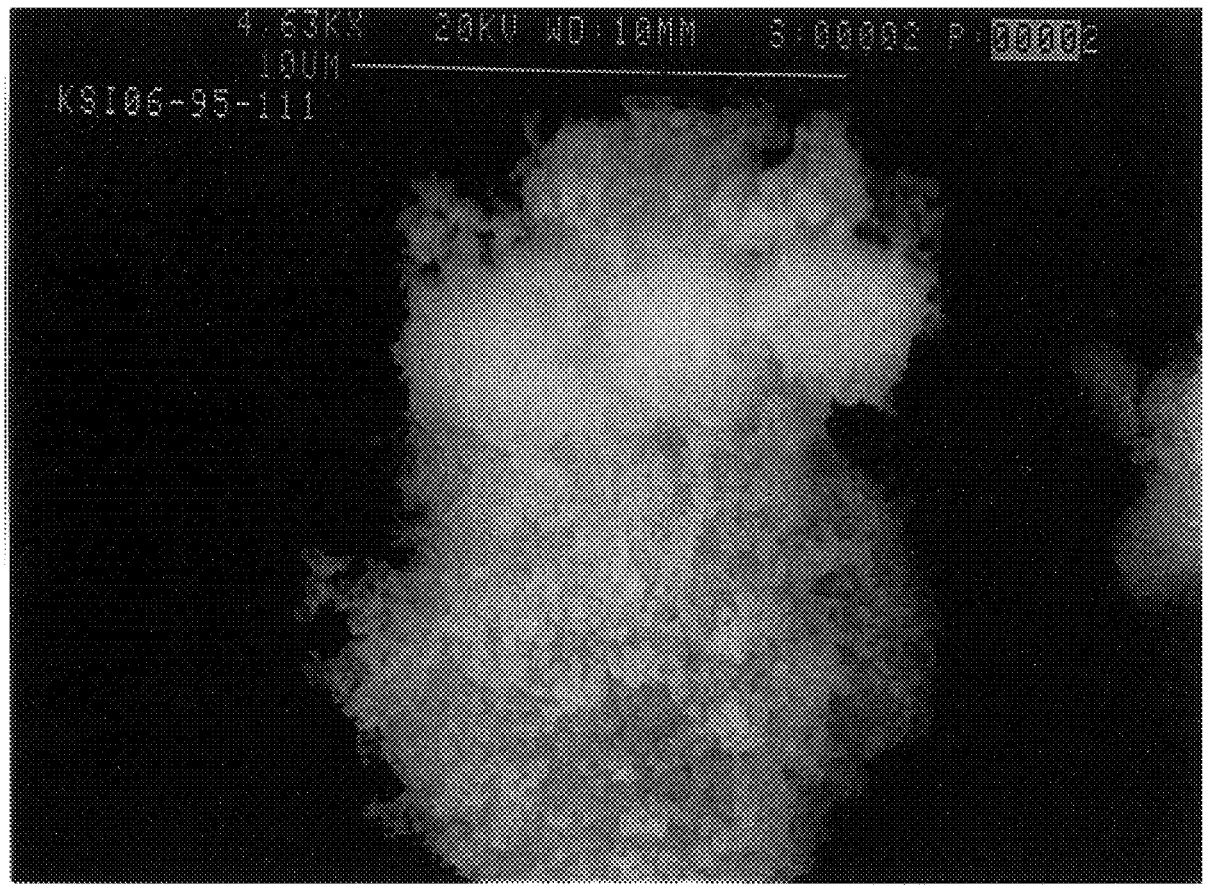
Figure 3C:
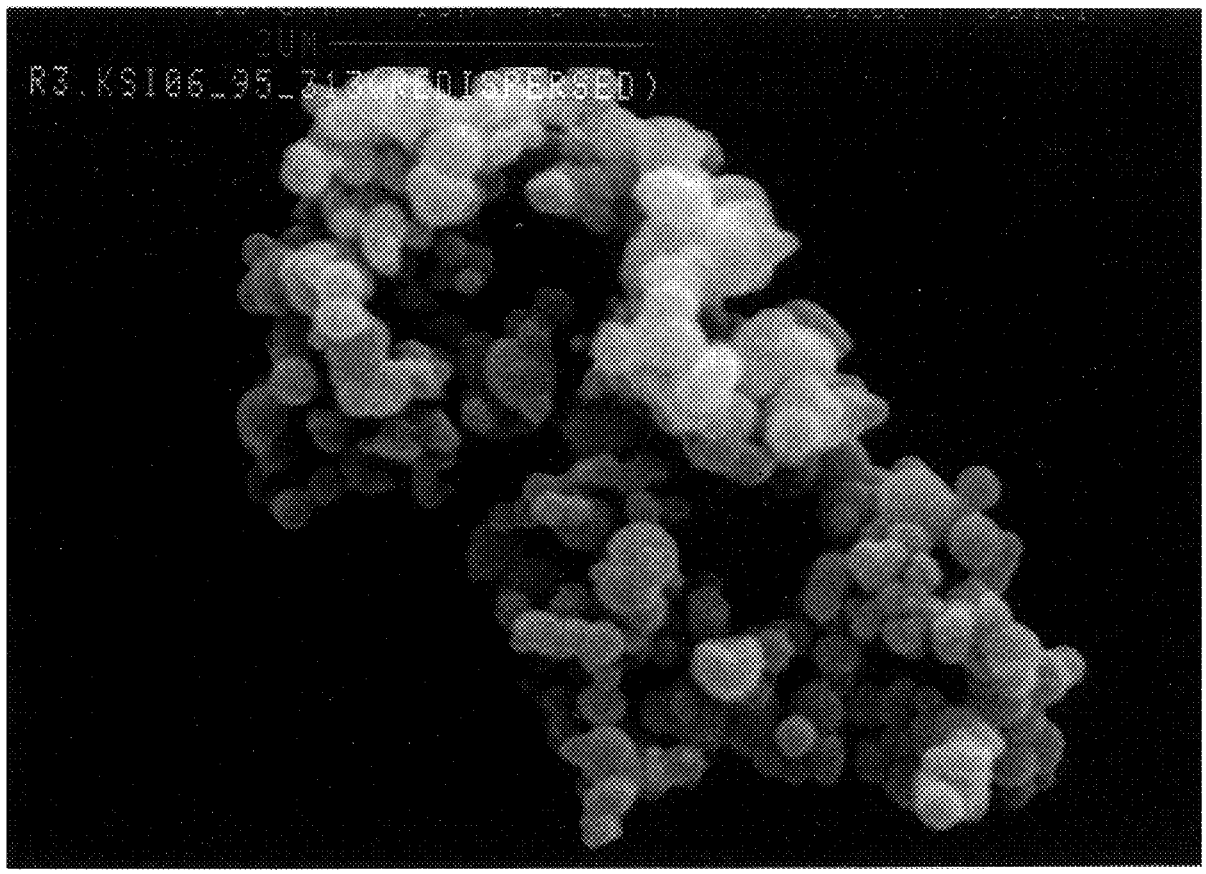

In FIGS. 3a to 3c are shown electron micrographs of calcium carbonate products produced by the process of the invention. In FIG. 3a, is shown uniform sized, dispersed crystals of PCC with a size, between about 0.1 and 0.2$\mu$. In FIG. 3b is shown a snowflake, i.e., an association of individual particles loosely aggregated, of flocculated uniform crystals of PCC, about 0.1$\mu$ to 0.2$\mu$ in size, The aggregate is about 10 $\mu$ which fosters settling. In FIG. 3c, which is an electron micrograph of the product of Example II, is shown snowflake of crystals, about 0.1 to 0.3 $\mu$ in size, after drying. The snowflake size is about 4 $\mu$.

While this invention has been described with reference to certain specific embodiments and examples, it will be recognized by those skilled in the art that many variations are possible without departing from the scope and spirit of this invention, and that the invention, as described by the claims, is intended to cover all changes and modifications of the invention which do not depart from the spirit of the invention.

What is claimed is:

1. A method for forming precipitated calcium carbonate comprising dissolving impure hydrated lime into an aqueous solution, separating solid materials from the dissolved hydrated lime to form a clear solution of calcium hydroxide, reacting the clear solution with carbon dioxide gas in cocurrent plug-flow reaction conditions to form a suspension of precipitated calcium carbonate.

2. A method as in claim 1 additionally comprising separating the calcium carbonate from the suspension.

3. A method as in claim 2 wherein the separating step comprises settling and decanting.

4. A method as in claim 2 wherein the separating step comprises filtering.

5. A method as in claim 2 wherein the separating step comprises centrifuging.

6. A method for controlling the reaction environment in a continuous reaction of calcium hydroxide and carbon dioxide to form calcium carbonate comprising;

directing a solution of calcium hydroxide free of solid-phase calcium hydroxide into a reaction zone, directing carbon dioxide-containing gas into the reaction zone, reacting essentially all of the calcium hydroxide in the solution with the carbon dioxide gas to form calcium carbonate by mixing the solution and the gas in the reaction zone to form a suspension of precipitated calcium carbonate while directing the solution and the gas together along an axis in the reaction zone in cocurrent plug-flow conditions.

7. A method as in claim 6 additionally comprising separating the precipitated calcium carbonate from the suspension by directing the suspension of calcium carbonate into a quiescent zone to allow the calcium carbonate crystals to settle from the suspension.

8. A method as in claim 6 additionally comprising separating the calcium carbonate from the suspension.

9. A method as in claim 8 wherein the separating step comprises settling and decanting.

10. A method as in claim 8 wherein the separating step comprises filtering.

11. A method as in claim 8 wherein the separating step comprises centrifuging.

12. A method as in claim 8 wherein flocculating agents are introduced to the suspended calcium carbonate to assist separation of the precipitated calcium carbonate from the suspension.

13. A method as in claim 8 wherein materials more soluble than calcium carbonate that remain in solution after formation of the precipitated calcium carbonate are removed from the calcium carbonate by directing the soluble materials in liquid solution from the separated calcium carbonate.

14. A method as in claim 6 wherein solid phase materials that are less soluble than calcium hydroxide in the solution free of solid-phase calcium hydroxide are separated from the solution before it is directed into the reaction zone.

15. A method as in claim 14 wherein the less soluble solid phase materials that are denser than the solution are separated by settling.

16. A method as in claim 14 wherein the less soluble solid phase materials that are denser than the solution are separated by centrifuging.

17. A method as in claim 14 wherein the less soluble solid phase materials that are less dense than the solution are separated by skimming.

18. A method as in claim 14 wherein the less soluble solid phase materials are separated by filtration.

19. A method as in claim 6 wherein the carbon-dioxide-containing gas is introduced at selected points along the axis from the beginning of the reaction zone.

20. A method as in claim 6 wherein the carbon-dioxide-containing gas is introduced at solely one point along the axis.

21. A method as in claim 6 wherein crystal morphology modifying agents are introduced to the solution of calcium hydroxide prior to any mixing of the solution with the carbon dioxide gas.

22. A method as in claim 6, wherein crystal morphology modifying agents are introduced at selected points along the axis.

23. A method as in claim 6 wherein crystal size modifying agents are introduced to the solution of calcium hydroxide prior to any mixing of the solution with the carbon dioxide gas.

24. A method as in claim 6, wherein crystal size modifying agents are introduced at selected points along the axis.

25. A method as in claim 6 wherein the time and reaction conditions are adjusted for formation of uniformly sized crystals such that after initial contact of the calcium hydroxide and carbon dioxide gas and formation of small crystals, calcium carbonate formation is predominately crystal growth as opposed to new crystal formation.

26. A method as in claim 25, wherein crystal morphology modifying agents are introduced at selected points along the axis.

27. A method as in claim 25, wherein crystal size modifying agents are introduced at selected points along the axis.

28. A method as in claim 6 wherein the time and reaction conditions are adjusted for formation of uniformly sized small crystals such that after initial contact of the calcium hydroxide and carbon dioxide gas and formation of small crystals, calcium carbonate formation is predominately formation of new small crystals as opposed to crystal growth of existing crystals.

29. A method as in claim 28, wherein crystal morphology modifying agents are introduced at selected points along the axis.

30. A method as in claim 28, wherein crystal size modifying agents are introduced at selected points along the axis.

31. A method for controlling the reaction environment in a continuous reaction of calcium hydroxide and a reagent to form a calcium product comprising;

directing a solution of calcium hydroxide free of solid-phase calcium hydroxide into a reaction zone, directing the reagent into the reaction zone, reacting essentially all of the calcium hydroxide in the solution with the reagent to form calcium product by mixing the solution and the reagent in the reaction zone to form a suspension of precipitated calcium product while directing the solution and the reagent together along an axis in the reaction zone in cocurrent plug-flow conditions, the calcium product having a solubility in the solution less than the solubility of calcium hydroxide.

32. A method as in claim 31 wherein the reagent and calcium product are selected from the group consisting of those shown in the table:

| Calcium Product | Reagent |
|---|---|
| Carbonate | $CO_2$ |
| Fluoride | HF |
| Oxalate | Oxalic Acid |
| Diorthphosphate | $H_3PO_4$. |

\* \* \* \* \*